United States Patent [19]

Li et al.

[11] Patent Number: 4,790,819

[45] Date of Patent: Dec. 13, 1988

[54] FIBRIN CLOT DELIVERY DEVICE AND METHOD

[75] Inventors: Lehmann K. Li, Fairfield; Russell F. Warren, Greenwich, both of Conn.; Steven P. Arnoczky, New York, N.Y.; Robert J. Bedard, Southbury, Conn.

[73] Assignee: American Cyanamid Company, Stamford, Conn.

[21] Appl. No.: 88,743

[22] Filed: Aug. 24, 1987

[51] Int. Cl.$^4$ .............................................. A61M 31/00
[52] U.S. Cl. ...................................... 604/59; 604/49; 604/218
[58] Field of Search ................ 604/51, 57, 59, 60, 604/11, 13, 15, 17, 207–211, 218

[56] References Cited

U.S. PATENT DOCUMENTS

| | | | |
|---|---|---|---|
| 3,153,496 | 10/1964 | Johnson | 604/207 |
| 3,506,008 | 4/1970 | Huck | 604/60 |
| 3,823,715 | 7/1974 | Holanek et al. | 604/59 |
| 3,828,987 | 8/1974 | Drummond et al. | 604/208 |
| 4,646,738 | 3/1987 | Trott | 128/305 |
| 4,674,500 | 6/1987 | De Satnick | 128/305 |

FOREIGN PATENT DOCUMENTS

| | | | |
|---|---|---|---|
| 0037920 | 10/1981 | European Pat. Off. | 604/218 |
| 0097503 | 2/1961 | Norway | 604/218 |

OTHER PUBLICATIONS

Arnoczky et al., "Meniscal Repair Using an Exogeneous Fibrin Clot-An Experimental Study", *Orthop Transactions* 1986: 10:327–328.

*Primary Examiner*—Dalton L. Truluck
*Assistant Examiner*—Denise Whelton
*Attorney, Agent, or Firm*—David A. Warmbold

[57] ABSTRACT

A delivery device for depositing an exogenous fibrin clot into a wound site during an arthroscopic surgical operation. The delivery device having a tubular body and plunger. The body including a large internal diameter collection chamber and a small internal diameter ejection chamber with an internal frusto-conical transition chamber positioned therebetween. The plunger having a rear tamping knob on one end and an ejection tip on the other end. The rear knob having a matching frusto-conical portion used for tamping the fibrin clot material from the collection chamber into the ejection chamber. The tip of the plunger being insertable into the injection chamber to push the fibrin clot material out of the delivery device. The plunger also having a forward stop knob which limits the depth of insertion of the plunger into the body. The tip of the plunger when fully inserted extends axially beyond the end of the ejection chamber. A method of depositing a fibrin clot material into a wound site during an arthroscopic operation is also disclosed.

9 Claims, 2 Drawing Sheets

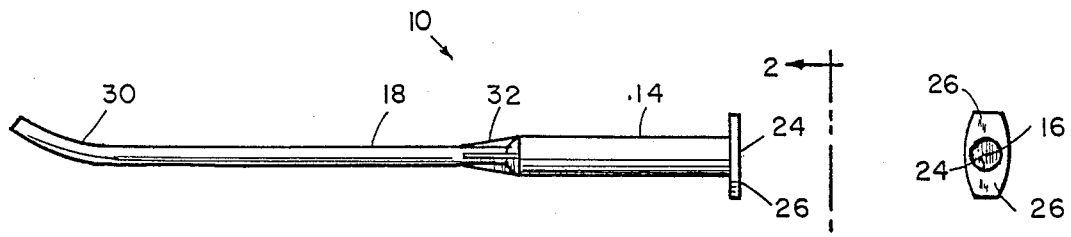
FIG. 1
FIG. 2
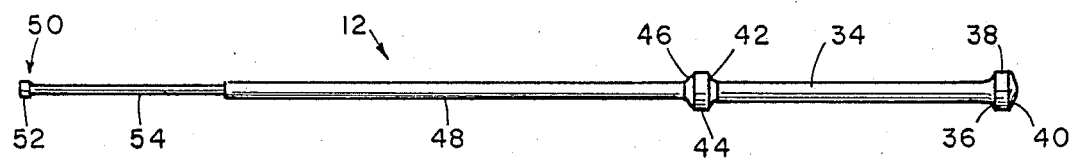
FIG. 3
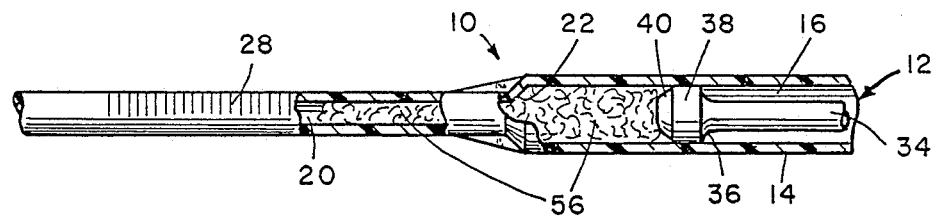
FIG. 4
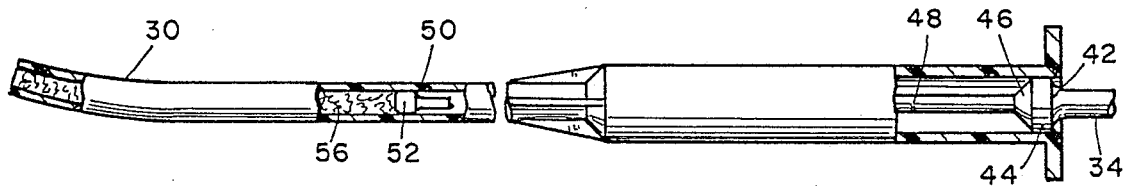
FIG. 5

FIBRIN CLOT DELIVERY DEVICE AND METHOD

FIELD OF THE INVENTION

This invention relates generally to an arthroscopic surgical device and a method of its use. More particularly, this invention discloses a surgical device and method for depositing an exogenous fibrin clot into a wound site during an arthroscopic surgical operation.

BACKGROUND OF THE INVENTION

The introduction of a hematoma or fibrin clot is an initial and essential phase in wound repair. The fibrin clot provides a matrix scaffold as well as a chemotactic stimulus to the various cellular elements involved in wound repair. Usually the hematoma or fibrin clot is a naturally occurring sequel in injury to vascular tissue. However, this fibrin clotting is absent in most injuries to articular cartilage and meniscus such as that found in knee, hip and elbow joints. Clinical and experimental observations have shown that meniscal tissue is capable of repair when exposed to vascular (bleeding) tissues and a recent study discusses the three primary avenues that have been used to date to improve the blood supply. These include resecting the peripheral white rim back to a bleeding capsular bed, using a biopsy needle to create radial perforations in the meniscus and using an arthroscopy rasp to abrade the superior and inferior parameniscal synovium to increase blood supply to the meniscal tear. These procedures have all been met with varying degrees of success with the use of the arthroscopic rasp providing the best results. See disclosure by C. E. Henning, M. A. Lynch and J. R. Clark, "Vascularity for Healing of Meniscus Repairs", *The Journal of Arthroscopic and Related Surgery* 3(1), 13–18 (1987).

Additionally, however, it has been determined that the insertion of an exogenous fibrin clot into the seam of a meniscal tear in dogs will aid in the healing of the articular cartilage and meniscus as disclosed by S. P. Arnoczky, C. A. McDevitt, R. F. Warren and J. Spivak, "Meniscal Repair Using an Exogenous Fibrin Clot—An Experimental Study in the Dog", *Orthop. Transactions* 1986:10:327–8. However, the viscosity of a fibrin clot is very thick. The material is gel-like and will not flow by itself. Therefore it is very difficult to place a bead of the fibrin clot material into a wound site during an arthroscopic operation. Known medical devices are not suitable or adaptable for use in the vicinity of an articulate joint to deposit a fibrin clot into an articulate joint area.

U.S. Pat. No. 3,506,008 issued to Huck shows a reuseable medical applicator which utilizes an internal rubber plug as an ejector. The plug does not extend beyond the body section such that a significant amount of medicament is left in the applicator even after the plug has been fully seated within the applicator body.

U.S. Pat. No. 3,823,715 issued to Holanek et al discloses a suppository introducer which is used to inject an extrudable material into an open orifice of the human body. The introducer is loaded through its front or small diameter opening. Once the device is inserted into the body, the material is then forced outwardly back through the front opening by a piston. No provision is made to provide a material collection area and the limit of travel of the plunger is controlled to prevent the piston from extending out of the front portion of the introducer.

In the above mentioned medical devices the particular placement of the medicament is not critical to the use of the device. However, often times in medical surgery the placement of the medicament within the patient is critical.

Accordingly, one of the objects of the present invention is to produce a fibrin clot delivery device which can precisely and easily place a fibrin clot material into a wound site during an arthroscopic surgery operation.

It is another object to produce a fibrin clot delivery device which is capable of placing a continuous bead of fibrin clot material into a wound site.

Still another object is to produce a fibrin clot delivery device which is small in size and able to work well in confined spaces such as found during a normal arthroscopic surgical operation.

A further object is to provide a fibrin clot delivery device which includes a collection chamber and a graduated ejection chamber such that the amount of fibrin clot material to be inserted can be premeasured before insertion of the device into the wound site.

Yet another object is to produce a fibrin clot deliery device which deposits a bead of fibrin clot material into a wound site without the material clinging to the end of the device.

It is a further important object of the present invention to provide a method of using fibrin delivery device to place a bead of gel-like material into a wound site through small slits made in the skin of a human body as performed during an arthroscopic surgical operation.

Another object of the present invention is to provide a method of depositing a fibrin clot material into a wound site which method involves steps that may be precisely, easily and safely carried out by a physician using one hand during an arthroscopic operation without the necessity of subjecting the patient to a major surgical operation.

SUMMARY OF THE INVENTION

These and other objects are achieved by providing a novel device which includes an elongated hollow applicator body and a plunger for depositing an exogenous fibrin clot into a wound site during an arthroscopic surgical operation.

The elongated applicator body has a large internal diameter cylindrical portion constituting a collection chamber and a small internal diameter cylindrical portion constituting an ejection chamber. A transition zone is formed between the collection chamber and ejection chamber. The transition zone is defined by a frusto-conical surface opening towards the collection chamber and acts as an internal stop for the plunger. The ejection chamber is graduated so that the amount of fibrin clot material being placed in the tube can be premeasured before insertion of the device into the wound site. The ejection chamber is further elongated so that the inserted end of the device is of sufficient length so that it may be positioned near the wound site during an arthroscopic surgery operation.

In one embodiment the frust-conical surface of the applicator body is angled approximately 45 degrees relative to the longitudinal axis of the applicator body. In another embodiment, the frusto-conical surface is angled less than 45 degrees and preferably in the range of 2 to 10 degrees relative to the longitudinal axis of the applicator body.

The plunger is provided with a cylindrical handle having a large diameter tamping knob at one end. The tamping knob has an external diameter slightly less than the internal diameter of the collection chamber. The tamping knob is used to tamp the fibrin clot material which was placed into the collection chamber into the ejection chamber. A second knob is provided on the other end of the handle a spaced distance from the tamping knob. The second knob also has an external diameter slightly smaller than the internal diameter of the collection chamber. Extending axially from the second knob is an elongated pusher rod with a rounded tip at its remote end. The tip has an external diameter slightly smaller than the internal diameter of the ejection chamber.

The second plunger knob acts as a stop to prevent over insertion of the plunger into the applicator body. The second knob is provided with a frusto-conical surface which faces the frusto-conical surface of the applicator body when the tip of the plunger is inserted into the ejection chamber. The length of the plunger from the second knob to the tip is slightly longer than the total axial length of the ejection chamber. Therefore, when the plunger is completely inserted within the applicator body the tip of the plunger will extend beyond the end of the ejection chamber to ensure that the fibrin clot material has been ejected from the device and that no material sticks or clings to the end of the device.

The surgical method includes the steps of performing arthroscopic surgery on a knee, hip or elbow joint by placing a mumber of small slits in the skin ajdacent the area of the joint. Then, positioning a number of hollow, flexible sleeves to extend from the interior surface of the patient's skin through the synovial layer into the articulate joint area. Viewing apparatus, which may preferably be an arthroscope, is positioned through the synovial layer in the vicinity of the sleeve devices. The physician inserts a number of cutting and suctioning tools into the wound site to repair the damage seen therein. Thereafter, the applicator body of the present invention, which has been filled with a pre-determined amount of fibrin clot material and has the plunger partially inserted therein, is inserted through one of the sleeve devices. The physician, while viewing the operation through an arthroscope, manipulates the applicator device with one hand to eject the fibrin clot material into the wound site where needed. The physician then removes the applicator device and stitches the wound site closed to complete the operation and allow the joint to heal.

BRIEF DESCRIPTION OF THE DRAWINGS:

Still other objects and features of the present invention will be more fully disclosed in the following detailed description of the preferred embodiment of the invention, which is to be considered together with the accompanying drawings, wherein:

FIG. 1 is an elevational view illustrating one embodiment of an applicator body made in accordance with the present invention;

FIG. 2 is a side plan view of a preferred form of the applicator body taken along line 2—2 of FIG. 1;

FIG. 3 is an elevational view illustrating one embodiment of a plunger made in accordance with the present invention;

FIG. 4 is a longitudinal sectional view of the fibrin clot delivery device showing the tamping end of the plunger being used to position the fibrin clot material into the ejection chamber;

FIG. 5, is a longitudinal sectional view of the fibrin clot delivery device with the tip of the plunger being inserted into the ejection chamber;

DETAILED DESCRIPTION OF THE PREFERRED EMBODIMENT

Figure 6:
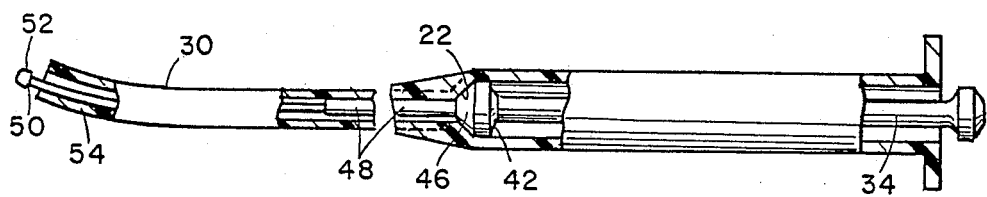
FIG. 6 is a longitudinal sectional view of the fibrin clot delivery device with the plunger fully inserted into the applicator body.

Referring now to FIGS. 1–4, there is shown an applicator body 10 and plunger 12 for depositing an exogenous fibrin clot into a wound site. In FIGS. 1 & 4, applicator body 10 has a first, rear large diameter cylindrical wall portion 14 defining a collection chamber 16 and a second, forward smaller diameter cylindrical wall portion 18 defining an ejection chamber 20. Cylindrical wall portions 14 and 18 are connected by a transitional frusto-conical shoulder portion 22 which opens toward the collection chamber 16. The rearward end of the collection chamber is open at 24 to permit insertion of the fibrin clot material and plunger 12. The shoulder portion 22 acts as a stop for plunger 12 to prevent over insertion of the plunger 12 into the applicator body 10. The rearward end of the large diameter wall portion 14 includes two outwardly extending radial flanges 26 as seen in FIGS. 1 and 2. These flanges extend radially in dimetrically opposed directions from each other to permit a physician to hook two fingers (not shown) around the flanges 26 to allow for easy handling of the applicator device.

The forward smaller diameter wall portion 18 is axially elongated to form a hollow tube to allow for insertion into a wound site during an arthroscopic operation. The ejection chamber 20 is graduated as shown at 28 to allow the physician to premeasure the amount of fibrin clot material inserted into the applicator body (see FIG. 4). The wall portion 18 of the ejection chamber 20 can be bent or curved at its forwardmost end as shown at 30 to facilitate placement of the fibrin clot material into the wound site. The bend 30 is preferably bent at an inclined angle of approximately 15 degrees relative to the longitudinal axis of ejection chamber 20. However, this angle is not critical to the operation of the applicator device and a full range of angles would work adequately well in providing for the insertion of the fibrin clot material into the wound site.

Referring to FIG. 1, the applicatory body 10 is shown provided with a plurality of external ribs 32 to strengthen the connection of the ejection chamber 20 to the large diameter wall portion 14 of the collection chamber 16.

In FIGS. 3 and 4, plunger 12 is shown provided with a cylindrical handle 34 having a large diameter rear cylindrical knob 36 on one end. Rear knob 36 is used for tamping the fibrin clot material into the ejection chamber 20. Rear knob 36 has a cylindrical portion 38 having an external diameter slightly smaller than the internal diameter of the rear wall portion 14 of collection chamber 16. The rear knob 36 has a frusto-conical surface portion 40 facing rearwardly away from cylindrical surface 38 of knob 36 (FIG. 3). When the plunger is turned around as shown in FIG. 4, the rear knob 36 can be inserted into the collection chamber 16 to inject the fibrin clot material from the collection chamber 16 to the ejection chamber 20. The angle of the frusto-conical surface portion 40 matches that of the frusto-conical surface portion 22 of applicator body 10 as that all of the fibrin clot material can be pushed into the ejection chamber 20.

Plunger 12 further includes a second large diameter knob 42 on the other end of handle 34 a spaced distance from the rear knob 36. The second or front knob 42 also has a cylindrical portion 44 having an external diameter slightly smaller than the internal diameter of the rear wall portion of the collection chamber 16. A frusto-conical portion 46 abuts the cylindrical portion 44 and acts as a transition from the large diameter knob 42 to an elongated smaller diameter plunger rod 48. The plunger rod 48 extends longitudinally a predetermined distance to a tip 50 at the frontal end of plunger 12. The tip 50 has a cylindrical portion 52 with an external diameter slightly smaller than the internal diameter of the ejection chamber 20.

The elongated plunger rod 48 also has a reduced diameter portion 54 immediately adjacent the tip 50. The redcued diameter portion 54 allows the tips 50 to more easily follow the bend 30 of the applicator body 10 without risk of breaking the plunger.

Referring to FIGS. 1-6 the frusto-conical surfaces 22, 40 and 46 are shown as inclined 45 degrees relative to the longitudinal axes of the applicator body 10 and plunger 12, respectively.

Referring to FIG. 4, the applicator body 10 and plunger 12 are shown with the rear knob 36 of the plunger being used to tamp an amount of fibrin clot material 56 from the collection chamber 16 to the graduated portion 28 of the ejection chamber 20. The fibrin clot material 56 was placed by hand into the collection chamber by the physician and the plunger 12 was reversed to that the rear or tamping knob 36 could be inserted into the collection chamber 16.

Referring to FIG. 5, the plunger 12 is shown being inserted into the applicator body 10 such that the tip 50 of plunger 12 is pushing the fibrin clot material 56 through the ejection chamber 20. The second knob 42 has entered the collection chamber 16 so that it centralizes the plunger rod 48 within the applicator body 10 to give the rod 48 added strength to prevent bending of the rod 48 during insertion into the applicator body 10.

In FIG. 6, the fibrin clot delivery device is shown with the plunger 12 completely inserted within the applicator body 10. The front knob 42 abuts the frusto-conical shoulder 22 of the applicator body 10 and the tip 50 extends outside the device to insure that all of the fibrin clot material has been ejected out of the device and so that none of the material clings to the open end of the ejection chamber 20.

Figure 7:
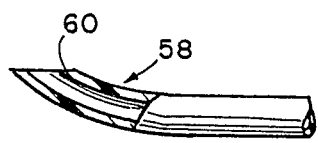
FIG. 7 is a plan view illustrating a modified form of the remote end of the ejection chamber to case placement of the fibrin clot material into the wound site.

FIG. 7 shows a modified form of the forward end 58 of the ejection chamber 20. The forward end 58 has been cut diagonally as shown at 60 to ease placement of the fibrin clot material into the wound site.

Figure 9:
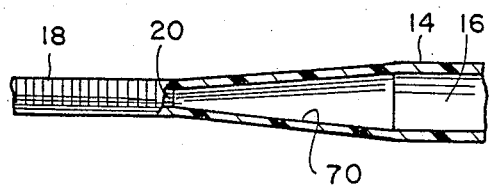
FIG. 9 is a partial cross-sectional view of the applicator body showing another embodiment of the transition zone.
Figure 10:
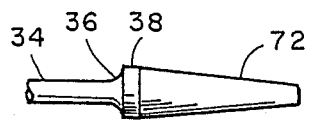
FIG. 10 is a partial plan view of the plunger showing another embodiment of the rear tamping knob.

With reference to FIGS. 9 and 10, a modified embodiment of the frusto-conical shoulder of body 10 and plunger 12 is shown. Like components shown in FIGS. 9 and 10 that are identical to those previously described in FIGS. 1 to 6 will be designated by the same reference characters. In FIG. 9, the large diameter wall portion 14 defining a collection chamber 16 and the small diameter wall portion 18 defining an ejection chamber 20 are shown. A new frusto-conical shoulder portion 70 is shown connecting the two respective wall portions 14 and 18. The frusto-conical surface 70 is shown as inclined at an angle of less than 45 degrees relative to the longitudinal axis of body 10. In this embodiment, the frusto-conical surface 70 is preferably angled between 2 and 10 degrees relative to the longitudinal axis of body 10. The more gradually tapered surface 70 provides for an easier delivery of a thixotropic material such as a fibrin clot from the collection chamber 16 to the ejection chamber 20.

In FIG. 10, the rear end of plunger 12 is shown. Handle 34 has a rear tamping knob 36 with cylindrical portion 38. The rear knob 36 has a frusto-conical surface portion 72 facing rearwardly away from cylindrical surface 38 of knob 36. The frusto-conical portion 72 is tapered to the same angle as surface 70 of body 10 so that all of the fibrin clot material to be pushed by the tamping knob 36 from the collection chamber 16 into the ejection chamber 20. The axial length of the frusto-conical portion 72 is equal to the axial length of the frusto-conical body surface 70. The shape of the front plunger knob 42 as shown in FIGS. 1-6 does not necessarily have to be changed and all other aspects of the invention remain the same.

The adapter body 10 of the fibrin clot delivery device is manufactured out of medical grade polycarbonate and cellulose acetate butyrate (CAB) tubing. The collection chamber 16 and flanges 26 are manufactured from the polycarbonate and the elongated ejection chamber 20 is manufactured from the CAB tubing. The plunger 12 is also made from the polycarbonate. The above materials represent the preferred construction materials, however, many other industrial type clear plastics would work equally well for the purposes of the present invention.

Figure 8:
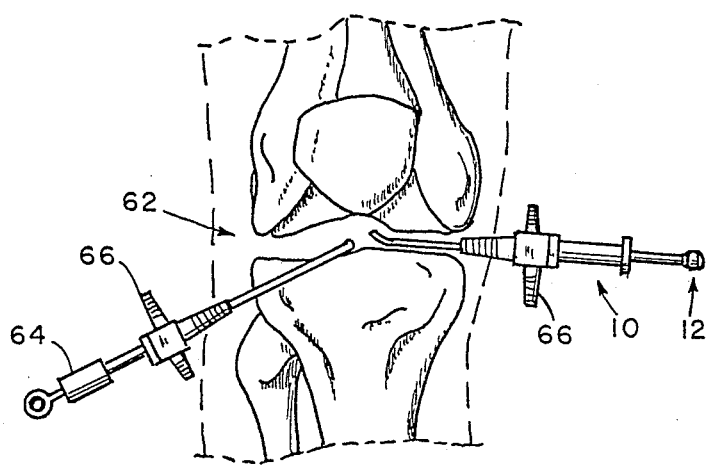
FIG. 8 is a perspective view of an articulate joint of a patient showing the fibrin clot delivery device of the instant invention positioned for depositing a bead of fibrin clot material in the wound site.

Referring to FIG. 8, a patient's knee joint 62 is shown undergoing a typical arthroscopic operation. An arthroscope 64 is shown in a lateral inferior insertion through the lateral infra patellar region of the knee joint 62. A sleeve or cannula 66 is inserted from the lateral region and has the applicator body 10 and plunger 12 of the fibrin delivery device inserted therethrough.

The surgical procedure includes making a numer of small slits in the skin of a patient. Positioning a number of flexible sleeves or crannulae 66 to extend from the arterior surface of the patient through the synovial layer into the articulate joint area. An arthroscope 64 is positioned through a crannula so that its lens is positioned at the wound site. Thereafter, the applicator body 10 of the present invention is inserted through a second crannula 66 such that the end of the elongated ejection chamber 20 is in the vicinity of the wound site. The applicator body 10 includes a premeasured quantity of fibrin clot material and has the plunger partially inserted therein. The physician then grasps the fibrin delivery device with one hand (not shown) and injects a quantity of fibrin clot material into the meniscle tear within the wound site. The physician can precisely place the fibrin clot material into the desired area by viewing the operation through the arthroscope 64. The physician then closes the meniscle tear with stitches and removes the devices from the wound site to allow healing.

The foregoing description of the invention has been presented for purposes of illustration and description and is not intended to be exhaustive or to limit the invention to the precise form disclosed. It was chosen and described in order to best explain the principles of the invention and their practical application to thereby enable others skilled in the art to best utilize the invention in various embodiments and with various modifications as are suited to the particular use contemplated. It is intended that the scope of the invention be defined by the claims appended hereto.

What is claimed:

1. A delivery device for depositing an exogenous fibrin clot into a wound site during an arthroscopic surgical operation comprising:
    a hollow body having a first large internal diameter cylindrical section constituting a collection chamber, a second smaller internal diameter cylindrical section constituting an ejection chamber; and an internal frusto-conical shoulder formed between the first and second cylindrical sections and opening toward the internal area of the collection chamber;
    a plunger having a cylindrical handle means, an enlarged diameter cylindrical knob on one end of the handle means, a plunger rod axially extending from the knob, and a cylindrical tip positioned at the remote end of the plunger rod, the knob having an outside diameter slightly smaller than the internal diameter of the collection chamber of said hollow body, the plunger tip having an outside diameter slightly smaller than the internal diameter of the hollow body ejection chamber, and the axial length of the plunger rod and tip being longer than the axial length of the hollow body ejection chamber such that upon insertion of said plunger into the hollow body the plunger tip will extend axially outside the ejection chamber when the knob of said plunger abuts the internal body shoulder; and the handle means of said plunger having a cylindrical tamping means positioned at the remote end of the handle means, the tamping means having a frusto-conical surface facing away from the knob of the handle means such that if said plunger is inserted tamping means first into said hollow body the frusto-conical surface of the tamping means will be facing towards the internal frusto-conical hollow body surface.

2. A fibrin clot delivery device according to claim 1, wherein the ejection chamber of said body and the plunger rod are axially elongated so that they may be inserted into a wound site through a small slit cut in a patient's skin as typically performed during an arthroscopic operation.

3. A fibrin clot delivery device according to claim 2, wherein the elongated cylindrical section of the ejection chamber is bent adjacent its remote end.

4. A fibrin clot delivery device according to claim 3, wherein the elongated plunger rod inlcudes a reduced diameter portion adjacent the tip to provide for easier insertion of the plunger tip through the bent portion of the ejection chamber.

5. A fibrin clot delivery clot device according to claim 1, wherein the ejection chamber of said body is marked with graduations so that the amount of fibrin clot material being inserted into said device can be accurately measured before insertion of said device into the wound site.

6. A fibrin clot delivery device according to claim 1, wherein the frusto-conical surfaces of the internal shoulder of the hollow body and the plunger knob and tamping means have angles of forty-five (45) degrees relative to the longitudinal axes of said applicator body and said plunger, resectively.

7. A fibrin clot delivery device according to claim 1, wherein the frusto-conical surfaces of the internal body shoulder and tamping plunger means have angles of less than 45 degrees relative to the longitudinal axes of said applicator body and plunger, respectively.

8. A fibrin clot delivery device according to claim 1, wherein the frusto-conical surfaces of the internal shoulder of said body and the tamper means of said plunger have angles in the range of 2 to 10 degrees relative to the longitudinal axes of said applicator body and plunger, respectively, to allow for easy delivery of a thixotropic material such as a fibrin clot from the collection chamber to the ejection chamber.

9. A surgical method of depositing an exogenous fibrin clot into an articulate joint of a patient during an arthroscopic operation to repair a meniscal tear comprising:
    cutting a preselected number of small incisions through the anterior surface into the synovial layer of an articulate joint of a patient;
    positioning a viewing apparatus through the synovial layer;
    inserting surgical instruments to repair the meniscal as found in said articulate joint;
    inserting a fibrin clot delivery device into the articulate joint to deposit an exogenous fibrin clot into the meniscal tear, the delivery device having a hollow body with a first large internal diameter cylindrical section constituting a collection chamber, said collection chamber having a fibrin clot therein, a second smaller internal diameter cylindrical section constituting an ejecting chamber, and an internal fruso-conical shoulder formed between the first and second cylindrical sections; and a plunger having a handle means, an enlarged diameter cylindrical knob on one end of the handle means and a cylindrical tamping means positioned at the outer end of the handle means, a plunger rod axially extending from the knob, and a cylindrical tip positioned at the remote end of the plunger rod, the knob having an outside diameter slightly smaller than the internal diameter of the collection chamber, the plunger rod being receivable into the ejection chamber, the plunger tip having an outside diameter slightly smaller than the internal diameter of the ejection chamber, and the axial length of the plunger rod and tip being longer than the axial length of the ejection chamber such that upon insertion of said plunger into the body the plunger tip will extend axially outside the ejection chamber when the knob of said plunger abuts the internal body shoulder;
    inserting the plunger into the hollow body with the tamping means leading;
    tamping the fibrin clot into the ejection chamber;
    removing the plunger;
    reinserting the plunger into the hollow body with the cylindrical tip leading whereby the fibrin clot is ejected from the ejection chamber; and
    stitching closed the meniscal tear, and removing all surgical instruments from the joint, and closing the small incisions to allow the joint to heal.

* * * * *